US007700314B2

(12) United States Patent
El-Tayar et al.

(10) Patent No.: US 7,700,314 B2
(45) Date of Patent: Apr. 20, 2010

(54) METHOD FOR PRODUCING POLYOL-IFN-β CONJUGATE

(75) Inventors: Nabil El-Tayar, Milton, MA (US); Michael J. Roberts, Madison, AL (US); Milton Harris, Huntsville, AL (US); Wayne Sawlivich, Wilmington, MA (US)

(73) Assignee: Merck Serono SA, Coinsins, Vaud (CH)

( * ) Notice: Subject to any disclaimer, the term of this patent is extended or adjusted under 35 U.S.C. 154(b) by 420 days.

(21) Appl. No.: 11/674,476

(22) Filed: Feb. 13, 2007

(65) Prior Publication Data
US 2007/0141620 A1 Jun. 21, 2007

Related U.S. Application Data

(60) Division of application No. 10/649,609, filed on Aug. 28, 2003, now Pat. No. 7,357,925, which is a division of application No. 09/698,133, filed on Oct. 30, 2000, now Pat. No. 6,638,500, which is a continuation of application No. PCT/US99/09161, filed on Apr. 28, 1999.

(60) Provisional application No. 60/083,339, filed on Apr. 28, 1998.

(51) Int. Cl.
*C12P 21/00* (2006.01)
*C08G 65/08* (2006.01)
*C07K 14/52* (2006.01)

(52) U.S. Cl. .......................... 435/68.1; 525/59; 525/61; 530/351

(58) Field of Classification Search ........................ None
See application file for complete search history.

(56) References Cited

U.S. PATENT DOCUMENTS

| | | | |
|---|---|---|---|
| 4,766,106 A * | 8/1988 | Katre et al. .................. 514/12 |
| 4,917,888 A | 4/1990 | Katre et al. |
| 5,166,322 A | 11/1992 | Shaw et al. |
| 5,206,344 A | 4/1993 | Katre et al. |
| 5,382,657 A | 1/1995 | Karasiewicz et al. |
| 5,711,944 A | 1/1998 | Gilbert et al. |
| 5,851,984 A * | 12/1998 | Matthews et al. ............ 514/2 |
| 5,986,265 A | 11/1999 | Kinstler et al. |
| 6,479,049 B1 | 11/2002 | Platz et al. |
| 6,531,122 B1 | 3/2003 | Pedersen et al. |

FOREIGN PATENT DOCUMENTS

| | | |
|---|---|---|
| EP | 0 593 868 A1 | 4/1994 |
| EP | 0 675 201 A1 | 10/1995 |
| EP | 0 690 127 A1 | 1/1996 |
| WO | WO 87/00056 | 1/1987 |
| WO | WO 96/21469 | 7/1996 |
| WO | WO 97/11957 | 4/1997 |
| WO | WO 98/32466 | 7/1998 |
| WO | WO 99/03887 | 1/1999 |

OTHER PUBLICATIONS

Goodson et al. Site-directed pegylation of recombinant interleukin-2 at its glycosylation site (1990), Biotechnology, vol. 8, pp. 343-.*
Mark et al. Site-specific mutagenesis of the human fiboblast interferon gene (1984), PNAS, vol. 81, pp. 5662-5666.*
Woghiren et a., "Protected thiol-polyethylene glycol: A new activated polymer for reversible protein modification", Bioconjugate Chem, 4:314-318 (1993)I.
Goodson et al., "Site-directed pegylation of recombinant interleukin-2 at its glycosylation site", Biotechnology, 8:343-346, (1990).
Burnham, "Polymers for delivering peptides and proteins", Am J. Hosp Pharm, 51:210-218 (1994).
Derynck et al., "Isolation and structure of a human fibroblast interferon gene", Nature, 285:542-547 (1980).
Shepard et al., "A single amino acid change in IFN-$\beta_1$ abolishes its antiviral activity", Nature, 294:563-565 (1981).
Mark et al., "Site-specific mutagenesis of the human fibroblast interferon gene", Proc. Natl. Acad. Sci. USA, 81:5662-5666 (1984).
Monkarsh et al., "Isolation of positional isomers of monopoly (ethylene glycol)ylated interferon/α-2a and the determination of their biochemical and biological characteristics", American Chemical Society, 15:207-216 (1997).
Johnson et al., How interferons fight disease, Scientific American, vol. 270(5)68-75 (1994).
Karpusas et al., The crystal structure of human interferon β at 2.2-Å resolution, PNAS 94:11813-11818 (Oct. 1997).

* cited by examiner

*Primary Examiner*—Christine J Saoud
*Assistant Examiner*—Jegatheesan Seharaseyon
(74) *Attorney, Agent, or Firm*—Browdy and Neimark, PLLC (57) ABSTRACT

PEG-IFN-β conjugates, where a PEG moiety is covalently bound to $Cys^{17}$ of human IFN-β, are produced by a process of site specific PEGylation with a thiol reactive PEGylating agent. A pharmaceutical composition and a method for treating infections, tumors and autoimmune and inflammatory diseases are also provided. The invention further relates to a method for the stepwise attachment of PEG moieties in series to a polypeptide, and more particularly to IFN-β.

7 Claims, 7 Drawing Sheets

METHOD FOR PRODUCING POLYOL-IFN-β CONJUGATE

CROSS-REFERENCE TO RELATED APPLICATION

The present application claims priority under 35 U.S.C.§119(e) from U.S. provisional application Ser. No. 60/083,339, the entire contents of which are hereby incorporated by reference.

FIELD OF THE INVENTION

The invention relates to polyol-IFN-β conjugates wherein a polyol unit is covalently bound to $Cys^{17}$. Further objects of the present invention are the process for their site-specific production as well as their use in the therapy, prognosis or diagnosis of bacterial infections, viral infections, autoimmune diseases and inflammatory diseases. The present invention further relates to a method for the stepwise attachment of two or more PEG moieties to a polypeptide.

BACKGROUND OF THE INVENTION

Human fibroblast interferon (IFN-β) has antiviral activity and can also stimulate natural killer cells against neoplastic cells. It is a polypeptide of about 20,000 Da induced by viruses and double-stranded PNAs. From the nucleotide sequence of the gene for fibroblast interferon, cloned by recombinant DNA technology, Derynk et al. (*Nature*, 285: 542-547, 1980) deduced the complete amino acid sequence of the protein. It is 166 amino acid long.

Shepard et al. (*Nature*, 294:563-565, 1981) described a mutation at base 842 (Cys-Tyr at position 141) that abolished its anti-viral activity, and a variant clone with a deletion of nucleotides 1119-1121.

Mark et al. (*Proc. Natl. Acad. Sci. U.S.A.*, 81(18):5662-5666, 1984) inserted an artificial mutation by replacing base 469 (T) with (A) causing an amino acid switch from Cys-Ser at position 17. The resulting IFN-β was reported to be as active as the 'native' IFN-β and stable during long-term storage (−70° C.)

Covalent attachment of the hydrophilic polymer polyethylene glycol, (PEG), also known as polyethylene oxide, (PEO), to molecules has important applications in biotechnology and medicine. In its most common form, PEG is a linear polymer having hydroxyl groups at each terminus:

HO—$CH_2$—$CH_2O(CH_2CH_2O)_n CH_2CH_2$—OH

This formula can be represented in brief as HO-PEG-OH, where it is meant that -PEG- represents the polymer backbone without the terminal groups:

"-PEG-" means "—$CH_2CH_2O(CH_2CH_2O)_n CH_2CH_2$—"

PEG is commonly used as methoxy-PEG-OH, (m-PEG), in which one terminus is the relatively inert methoxy group, while the other terminus is a hydroxyl group that is subject to chemical modification.

$CH_3O$—$(CH_2CH_2O)_n$—$CH_2CH_2$—OH

Branched PEGs are also in common use. The branched PEGs can be represented as $R(\text{-PEG-OH})_m$ in which R represents a central core moiety such as pentaerythritol or glycerol, and m represents the number of branching arms. The number of branching arms (m) can range from three to a hundred or more. The hydroxyl groups are subject to chemical modification.

Another branched form, such as that described in PCT patent application WO 96/21466, has a single terminus that is subject to chemical modification. This type of PEG can be represented as $(CH_3O\text{-PEG-})_p R$—X, whereby p equals 2 or 3, R represents a central core such as lysine or glycerol, and X represents a functional group such as carboxyl that is subject to chemical activation. Yet another branched form, the "pendant PEG", has reactive groups, such as carboxyl, along the PEG backbone rather than at the end of PEG chains.

In addition to these forms of PEG, the polymer can also be prepared with weak or degradable linkages in the backbone. For example, Harris has shown in U.S. patent application Ser. No. 06/026,716 that PEG can be prepared with ester linkages in the polymer backbone that are subject to hydrolysis. This hydrolysis results in cleavage of the polymer into fragments of lower molecular weight, according to the reaction scheme:

-PEG-$CO_2$-PEG-+$H_2O$--PEG-$CO_2$H+HO-PEG-

According to the present invention, the term polyethylene glycol or PEG is meant to comprise all the above described derivatives.

The copolymers of ethylene oxide and propylene oxide are closely related to PEG in their chemistry, and they can be used instead of PEG in many of its applications. They have the following general formula:

HO—$CH_2CHRO(CH_2CHRO)_n CH_2CHR$—OH wherein R is H or $CH^3$.

PEG is a useful polymer having the property of high water solubility as well as high solubility in many organic solvents. PEG is also non-toxic and non-immunocgenic. When PEG is chemically attached (PEGylation) to a water insoluble compound, the resulting conjugate generally is water soluble, as well as soluble in many organic solvents.

PEG-protein conjugates are currently being used in protein replacement therapies and for other therapeutic uses. For example, PEGylated adenosine deaminase (ADAGEN®) is being used to treat severe combined immunodeficiency disease (SCIDS), PEGvlated L-asparaginase (ONCAPSPAR®) is being used to treat acute lymphoblastic leukemia (ALL), and PEGylated interferon-α (INTRON(R) A) is in Phase III trials for treating hepatitis C.

For a general review of PEG-protein conjugates with clinical efficacy see N. L. Burnhamr *Am. J. Hosp. Pharm.*, 15:210-218, 1994.

A variety of methods have been developed to PEGylate proteins. Attaching PEG to reactive groups zound on the protein is typically done utilizing electrophilically activated PEG derivatives. Attaching PEG to the α- and ε-amino groups found on lysine residues and the N-terminus results in a conjugate consisting of a mixture of products.

Generally, such conjugates consist of a population of the several PEG molecules attached per protein molecule ("PEG-mers") ranging from zero to the number of amino groups in the protein. For a protein molecule that has been singly modified, the PEG unit may be attached at a number of different amine sites.

This type of non-specific PEGylation has resulted in a number of conjugates that become almost inactive. Reduction of activity is typically caused by shielding the protein's active binding domain as is the case with many cytokines and antibodies. For example, Katre et al. in U.S. Pat. No. 4,766,106 and U.S. Pat. No. 4,917,888 describe the PEGylation of IFN-β and IL-2 with a large excess of methoxy-polyethylene glycolyl N-succinimidyl glutarate and methoxy-polyethylene glycolyl N-succinimidyl succinate. Both proteins were produced in microbial host cells, which allowed the site-specific mutation of the free cysteine to a serine. The mutation was necessary in microbial expression of IFN-β to facilitate protein folding. In particular, the IFN-β used in these experiments is the commercial product Betaseron®, in which $Cys^{17}$ residue is replaced with a serine. Additionally, the absence of glycosylation reduced its solubility in aqueous solution. Non-specific PEGylation resulted in increased solubility, but a major problem was the reduced level of activity and yield.

European Patent Application EP 593 868, entitled PEG-Interferon Conjugates, describes the preparation of PEG-IFN-α conjugates. However, the PEGylation reaction is not site-specific, and therefore a mixture of positional isomers of PEG-IFN-α conjugates are obtained (see also Monkar-sh et al., *ACS Svmp. Ser.*, 680:207-216, 1997.

Kinstler el al. in Eurooeap Patent App-lication EP 675 201 demonstrated the selective modification of the N-terminal residue of megakaryocyte growth and development factor (MGDF) with mPEG-propionaldehyde. This allowed for reproducible PEGylation and pharmacokinetics from lot to lot. Gilbert et al. in U.S. Pat. No. 5,711,944 demonstrated that PEGylation of IFN-α with an optimal level of activity could be produced. In this instance a laborious purification step was needed to obtain the optimal conjugate.

The majority of cytokines, as well as other proteins, do not possess a specific PEG attachment site and, apart from the examples mentioned above, it is very likely that some of the isomers produced through the PEGylation reaction be partially or totally inactive, thus causing a loss of activity of the final mixture.

Site-specific mono-PEGylation is thus a desirable goal in the preparation of such protein conjugates.

Woghiren et al. in *Bioconjugate Chem.*, 4(5):314-318, 993, synthesized a thiol-selective PEG derivative for such a site-specific PEGylation. A stable thiol-protected PEG derivative in the form of an parapyridyl disulfide reactive group was shown to specifically conjugate to the free cysteine in the protein, papain. The newly formed disulfide bond between papain and PEG could be cleaved under mild reducing conditions to regenerate the native protein.

Citation of any document herein is not intended as an admission that such document is pertinent prior art, or considered material to the patentability of any claim of the present application. Any statement as to content or a date of any document is based on the information available to applicants at the time of filing and does not constitute an admission as to the correctness of such a statement.

SUMMARY OF THE INVENTION

In the present invention, polyol-IFN-β conjugates, and particularly PEG-IFN-β conjugates, are provided wherein a polyol unit is covalently bound to $Cys^{17}$ The specific conjugation is obtained by allowing a thiol-reactive polyol agent to react with the Cys17 residue in IFN-β. Such conjugates are expected to show increased effectiveness in vivo. The aim is to obtain increased solubility at neutral pH, increased stability (decreased aggregation) decreased immunogenicity, and no loss of activity with respect to 'native' IFN-β. The results of such conjugation would decrease the number of doses for an intended effect, simplify and stabilize the formulation of a pharmaceutical composition, and possibly increase the long-term efficacy.

The present invention further provides a method for the stepwise attachment of PEG moieties in series to a polypeptide.

BRIEF DESCRIPTION OF THE DRAWINGS

FIGS. 2A-2C show the purification of the PEG-IFN-β conjugate carried out by size exclusion chromatography (Superose 12): FIG. 2A–first pass; FIG. 2B–second pass; FIG. 2C–third pass.

DETAILED DESCRIPTION OF THE INVENTION

The present invention is based on the discovery that the attachment of a polyol moiety, more specifically a PEG moiety, to the $Cys^{17}$ residue of human IFN-β unexpectedly increased (or at least retained and did not result in a decrease) the IFN-β biological activity from that of native human interferon-β. Thus, not only does IFN-β with a polyol moiety attached to the $Cys^{17}$ residue exhibit the same or increased IFN-β biological activity but this polyol-IFN-β conjugate also provides the desirable properties conferred by the polyol moiety, such as increased solubility.

"IFN-β", as used herein, means human fibroblast interferon, as obtained by isolation from biological fluids or as obtained by DNA recombinant techniques from prokaryotic or eukaryotic host cells as well as its salts, functional derivatives, precursors and active fractions, provided that they contain the cysteine residue appearing at position 17 in the naturally occurring form.

The polyol moiety in the polyol-IFN-β conjugate according to the present invention can be any water-soluble mono- or bifunctional poly(alkylene oxide) having a linear or branched chain. Typically, the polyol is a poly(alkylene glycol) such as poly(ethylene glycol) (PEG). However, those of skill in the art will recognize that other polyols, such as, for example poly (propylene glycol) and copolymers of polyethylene glycol and polypropylene glycol, can be suitably used.

As used herein, the term "PEG moiety" is intended to include, but is not limited to, linear and branched PEG, methoxy PEG, hydrolytically or enzymatically degradable PEG, pendant PEG, dendrimer PEG, copolymers of PEG and one or more polyols, and copolymers of PEG and. PLGA (poly (lactic/glycolic acid))

The definition "salts" as used herein refers both to salts of the carboxyl-groups and to the salts of the amino functions Of the compound obtainable through known methods. The salts of the carboxyl-groups include inorganic salts as, for example, sodium, potassium; calcium salts and salts with organic bases as those formed with an amine as triethanolamine, arginine or lysine. The salts of the amino groups included for example, salts with inorganic acids as hydrochloric acid and with organic acids as acetic acid.

The definition "functional derivatives" as herein used refers to derivatives which can be prepared from the functional groups present on the lateral chains of the amino acid moieties or on the terminal N- or C- groups according to known methods and are included in the present invention when they are pharmaceutically acceptable, i.e., when they do not destroy the protein activity or do not impart toxicity to the pharmaceutical compositions containing them. Such derivatives include for example esters or aliphatic amides of the carboxyl-groups and N-acyl derivatives of free amino groups or O-acyl derivatives of free hydroxyl-groups and are formed with acyl-groups as for example alcanoyl- or aroyl-groups.

The "precursors" are compounds which are converted into IFN-β in the human or animal body.

As "active fractions" of the protein, the present invention refers to any fragment or precursor of the polypeptidic chain of the compound itself, alone or in combination with related molecules or residues bound to it, for example, residues of sugars or phosphates, or aggregates of the polypeptide molecule when such fragments or precursors show the same activity of IFN-β as medicament.

The conjugates of the present invention can be prepared by any of the methods known in the art. According to an embodiment of the invention, IFN-β is reacted with the PEGylating agent in a suitable solvent and the desired conjugate is isolated and purified, for example, by applying one or more chromatographic methods.

"Chromatoqranhic method" means any technique that is used to separate the components of a mixture by their application on a support (stationary phase) through which a solvent (mobile phase) flows. The separation principles of the chromatography are based on the different physical nature of stationary and mobile phase.

Some particular types of chromatographic methods, wnich are well-known in the literature, include: liquid, high pressure liquid, ion exchange, absorption, affinity, partition, hydrophobic, reversed phase, gel filtration, ultrafiltration or thin-layer chromatography.

The "thiol-reactive PEGylating agent", as used in the present application, means any PEG derivative which is capable of reacting with the thiol group of the cysteine residue. It can be, for example, PEG containing a functional group such as orthopyridyl disulfide, vinylsulfone, maleimide, iodoacetimide, and others. According to a preferred embodiment of the present invention, the thiol-reactive PEGylating agent is the orthopyridyl disulfide (OPSS) derivative of PEG.

The PEGylating agent is used in its mono-methoxylated form where only one terminus is available for conjugation, or in a bifunctional form where both termini are available for conjugation, such-as for example in forming a conjugate with two IFN-β covalently attached to a single PEG moiety. It has preferably a molecular weight between 500 and 100,000.

A typical reaction scheme for the preparation of the conjugates of the invention is presented below:

The second line of the above scheme reports a method for cleaving the PEG-protein linkage The mPEG-OPSS derivative is highly selective for free sulphydryl groups and reacts rapidly under acidic pH conditions where the IFN-β is stable. The high selectivity can be demonstrated from the reduction of the conjugate to the native form of IFN-β and PEG.

The disulfide bond that is produced between the protein and PEG moieties has been shown to be stable in the circulation, but it can be reduced upon entering the cell environment. Therefore it is expected that this conjugate, which does not enter the cell, will be stable in the circulation until it is cleared.

It should be noted that the above reaction is site-specific because the other two Cys residues appearing at positions 31 and 141 in the naturally occurring form of human IFN-β do not react with the thiol-reactive PEGylating agent since they form a disulfide bridge.

The present invention is also directed to a method for the stepwise attachment of two or more PEG moieties to a polypeptide. This method is based upon the recognition that a low molecular weight activated PEG reacts more completely with a sterically hindered reaction site on a protein than does a high molecular weight activated PEG. PEG-modification of expensive therapeutic proteins must be cost effective in order for the production of the PEG conjugate to be practical. In addition, in order to reduce glomerular filtration and optimize the pharmacological properties of the PEG-protein conjugate, the conjugate should have an effective size equivalent to that of a protein with a molecular weight of 70 kDa. This means that for a site specific modification where one PEG will be attached, a PEG derivative having a molecular weight of greater than 20 kDa is preferably attached. If the site of modification is sterically crowded, the reactive group on the large PEG moiety may have difficulty reaching the modification site and thus will lead to low yields. A preferred method of PEGylating a polypeptide according to the present invention increases the yield of site-specific PEGylation by first attaching a small hetero or homobifunctional PEG moiety that, due to its relatively smaller size, can react with sterically crowded sites. Subsequent attachment of a large molecular weight PEG derivative to the small PEG results in a high yield of the desires PEGylated protein.

The method for sterwise attachment of two or more PEG moieties in series to a polypeptide according to the present invention includes attaching a low molecular weight heterbifunctional or homobifunctional PEG moiety first to the polypeptide and then attaching a monofunctional or bifunctional PEG moiety to the free terminus of the low molecular weight PEG moiety that is attached to the polypeptide. Following the stepwise attachment of two or more PEG moieties in series to a polypeptide, which polypeptide is preferably IFN-β and where $Cys^{17}$, located in a sterically crowded site, is the preferred site of PEG attachment, the PEG-polypeptide conjugate can be turified using one or more of the purification techniques such as ion exchange chromatography, size exclu- sion chromatography, hydrophobic interaction chromatography, affinity chromatocraphy, and reverse phase chromatography.

The low molecular weight PEG moiety has the formula:

where W and X are groups that independently react with an amine, sulfhydryl, carboryl or hydroxyl functional group to attach the low molecular weight PEG moiety to the polypeptide. W and X are preferably independently selected from orthopyridyl disulfide, maleimides, vinyl sulfones, iodoacetamides, amines, thiols, carboxyls, active esters, benzotriazole carbonates, p-nitrophenol carbonates, isocyanates, and biotin. The low molecular weight PEG moiety preferably has a molecular weight in the range of about 100 to 5,000 daltons.

The monofunctional or bifunctional PEG moiety for attachment to the free terminus of a low molecular weight PEG that is attached to the polypeptide has preferably a molecular weight in the range of about 100 daltons to 200 kDa and is preferably a methoxy PEG, branched PEG, hydrolytically or enzymatically degradable PEG, pendant PEG, or dendrimer PEG. The monofunctional or bifunctional PEG furthermore has the formula:

where Y is reactive to a terminal group on the free terminus of the low molecular weight PEG moiety that is attacned to the polypeptide and Z is —OCH$_3$ or a group reactive with to form a bifunctional conjugate.

The PEG-polypeptide conjugate produced by the above method for stepwise attachment of two or more PEG moieties can be used to produce a medicament or pharmaceutical composition for treating diseases or disorders for which the polypeptides is effective as an active ingredient.

Another object of the present invention is to provide the conjugates in substantially purified form in order for them to be suitable for use in pharmaceutical compositions, as active ingredient for the treatment, diagnosis or prognosis of bacterial and viral infections as well as autoimmune, inflammatory diseases and tumors. Such pharmaceutical compositions represent a further object of the present invention.

Non-limiting examples of the above-mentioned diseases include: septic shock, AIDS, rheumatoid arthritis, lupus erythematosus and-multiple sclerosis.

Further embodiments and advantages of the invention will be evident in the following description.

An embodiment of the invention is the administration of a pharmacologically active amount of the conjugates of the invention to subjects at risk of developing one of the diseases reported above or to subjects already showing such pathologies.

Any route of administration compatible with the active principle can be used. Parenteral administration, such as subcutaneous, intramuscular or intravenous injection is preferred. The dose of the active ingredient to be administered depends on the basis of the medical prescriptions according to age, weight and the individual response of the patient.

The dosage can be between 10 μg and 1 mg daily for an average body weight of 75 kg, and the preferable daily dose is between 20 μg and 200 μg.

The-pharmaceutical composition for narenteral administration can be prepared in an injectable forma comprising the active principle and a suitable vehicle. Vehicles for the parenteral administration are well known in the art and include, for example, water, saline solution, Pinger solution and/or dextrose. The vehicle can contain small amounts of excipients in order to maintain the stability and isotonicity of the pharmaceutical preparation. The preparation of the solutions can be carried out according to the ordinary modalities.

The present invention has been described with reference to the specific embodiments, but the content of the description comprises all modifications and substitutions which can be brought by a person skilled in the art without extending beyond the meaning and purpose of the claims.

The invention will now be described by means of the following Examples, which should not be construed as in any way limiting the present invention.

EXAMPLE 1

Preparation of PEG-IFN-β Conjugate

Modification of IFN-β with mPEG$_{5K}$-OPSS

Figure 1:
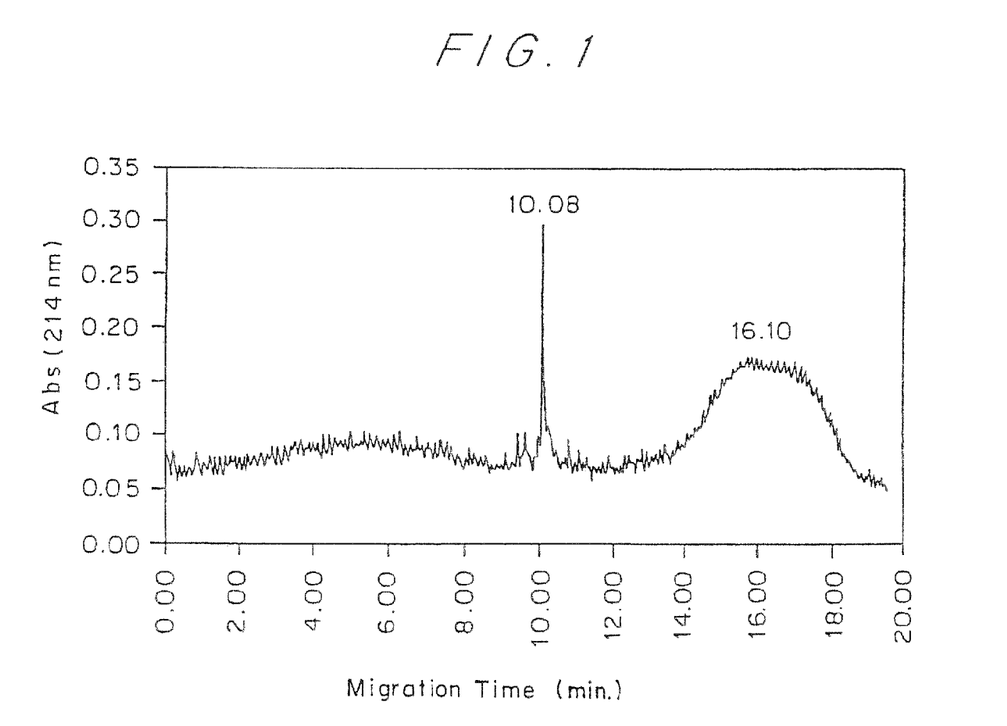
FIG. 1 shows the Capillary Electrophoresis (CE) graph of the PEG-IFN-β conjugate prior to purification.
Figure 2A:
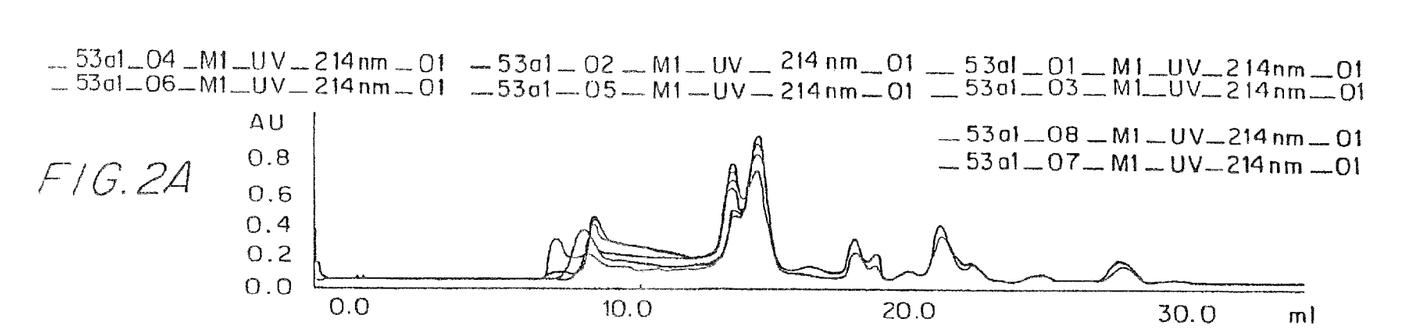
Figure 2B:
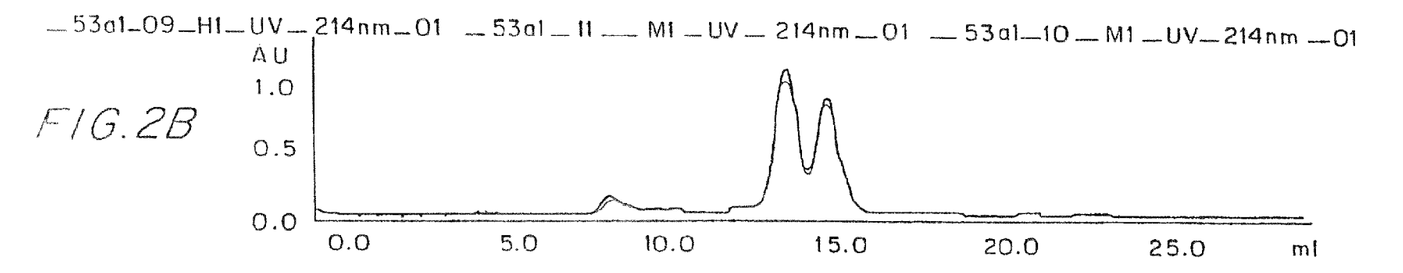
Figure 2C:
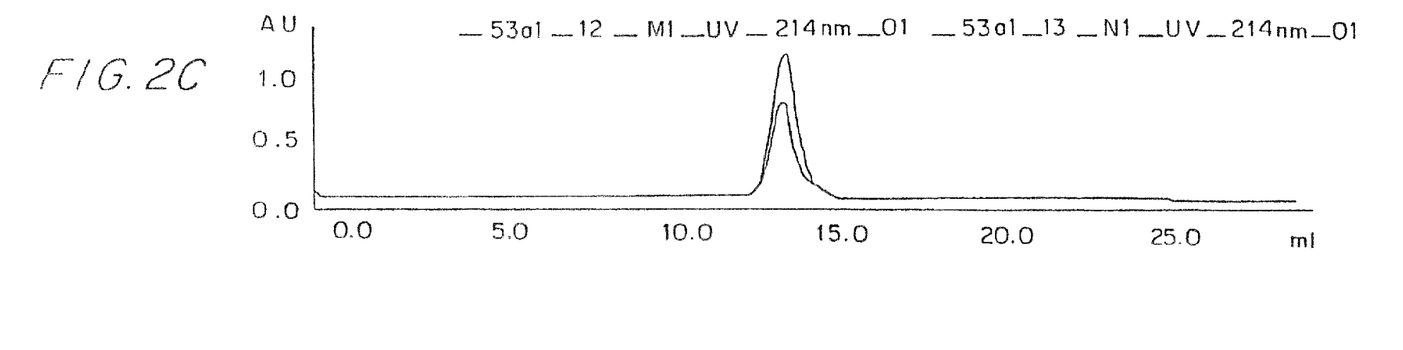
Figure 3:
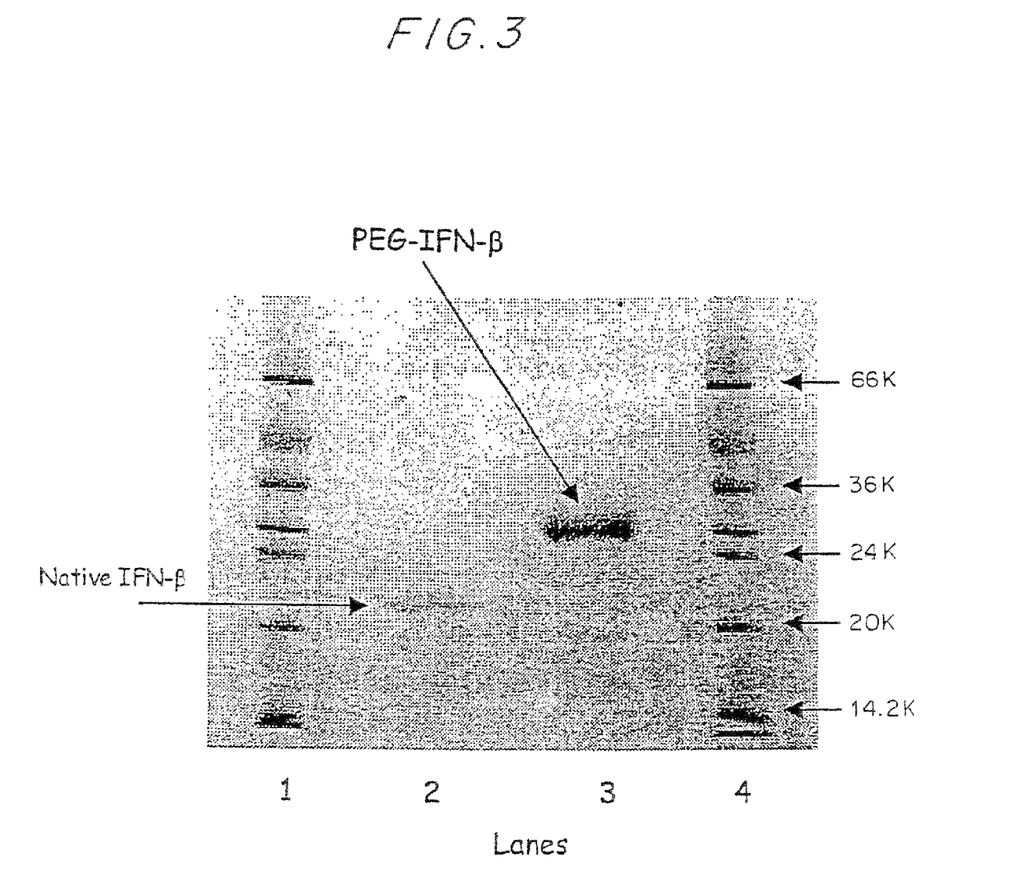
FIG. 3 shows the SDS-PAGE chromatography of purified PEG-IFN-β conjugate from the third pass of chromatography. Lanes 1 and 4 are protein molecular weight standards, lane 2 is "natives" IFN-β, and lane 3 is PEG-IFN-β conjugate.
Figure 4:
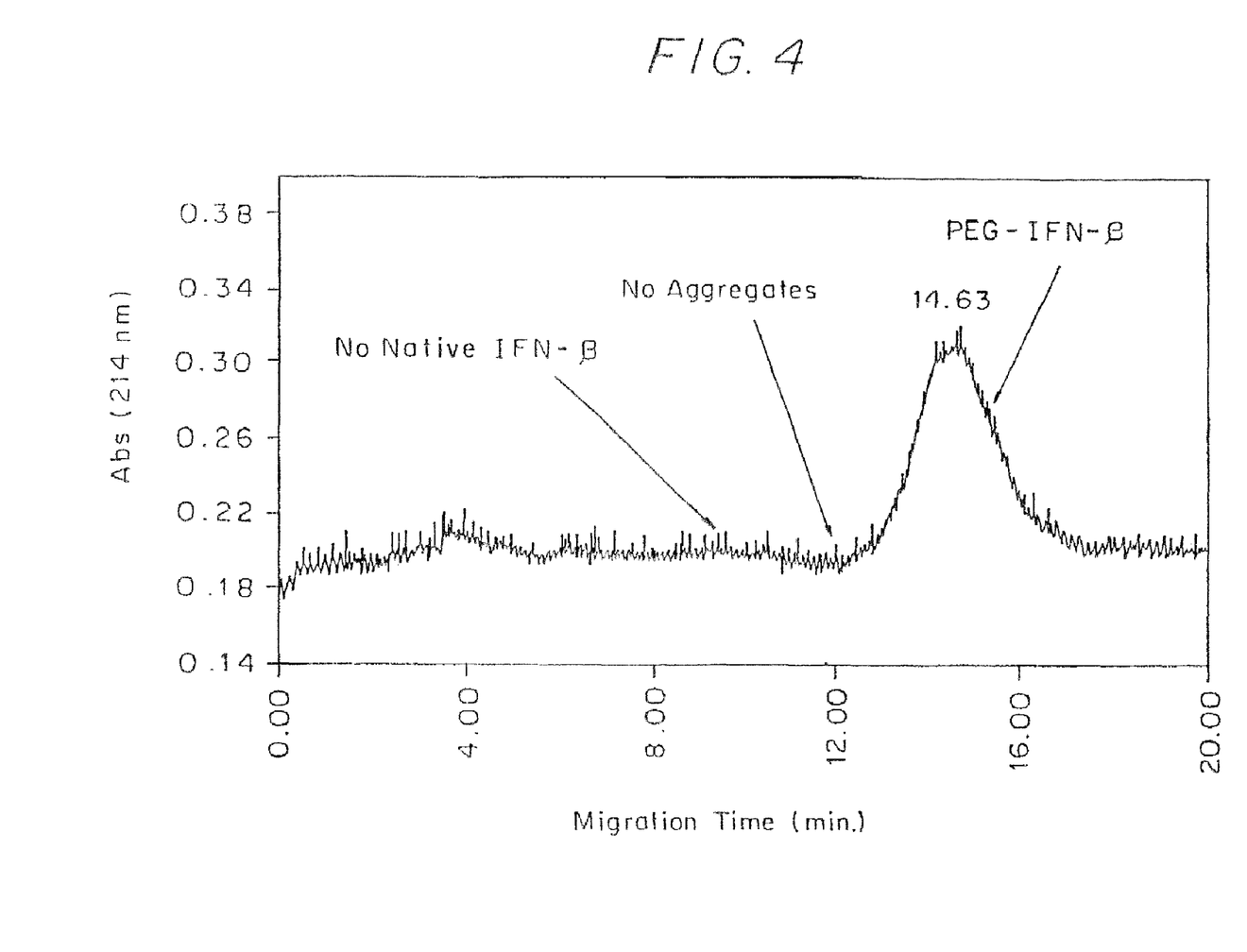
FIG. 4 reports the Capillary Electrophoresis (CE) graph of purified PEG-IFN-β conjugate in which IFN-β is PEGylated with mPEG-OPSS$_{5k}$.
Figure 5:
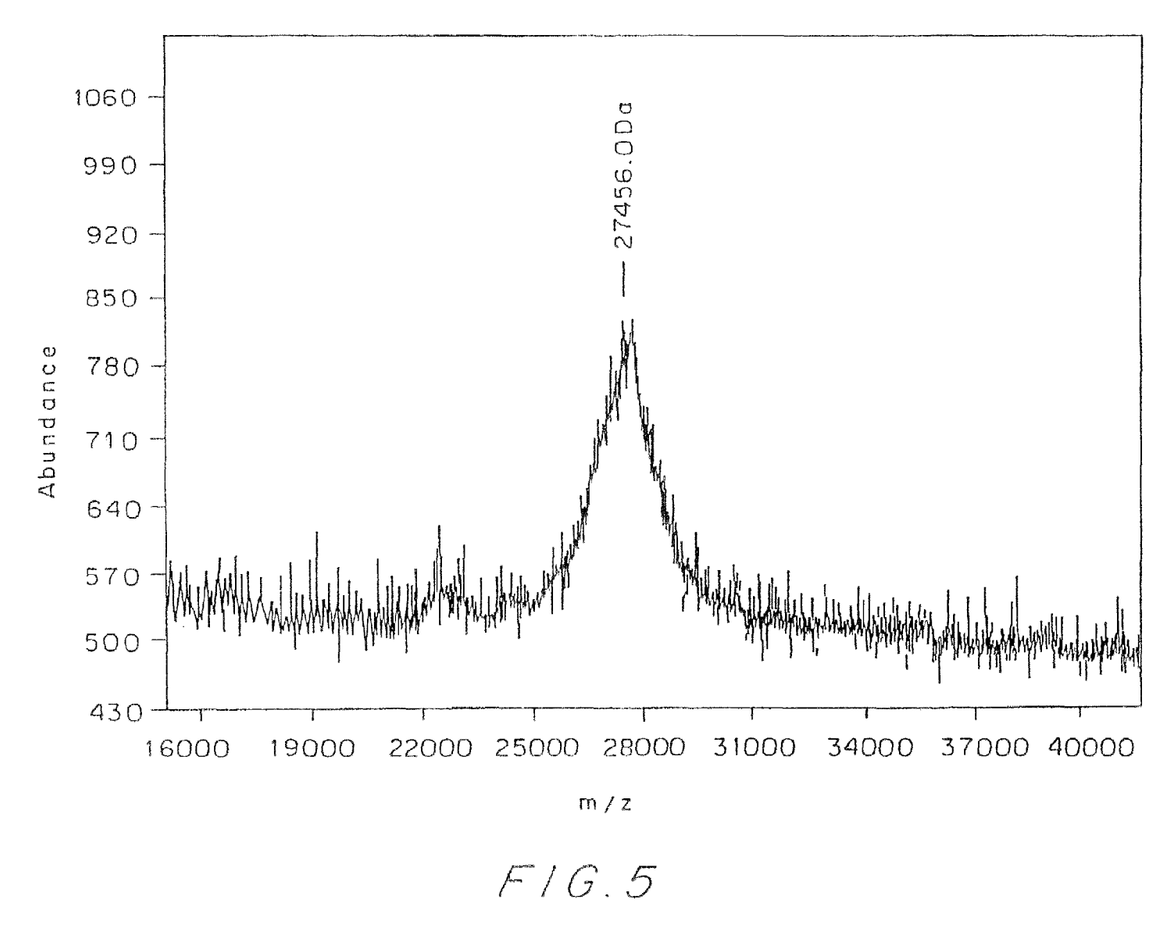
FIG. 5 reports the MALDI MS spectrum of purified PEG-IFN-β conjugate.

Recombinant human IFNβ, stable at a concentration of 0.37 mg/ml in 50 mM sodium acetate buffer, pH 3.6, was used for the preparation of a PEG-IFN-β conjugate. Approximately 1.0 ml of 6 M urea was added to 2 ml of IFN-β at a concentration of 0.37 mg/ml (0.74 mg, 3.7×1$^{-8}$ moles). mPEG$_{5K}$-OPSS was added in a molar excess of 50 moles to one mole of IFN-β and the two were allowed to react in a polypropylene vial for either 2 hours at 37° C. or 1 hour at 50° C. The reaction mixture was analyzed with Capillary Electrophoresis (CE) graph to determine the extent of PEG-IFN-β conjugate formation by the PEGylation reaction prior to any purification (FIG. 1). A typical yield for this reaction is 50% PEG-IFN-β. The reaction products were filtered from the reaction mixture with a 0.22 mm syringe filter and the filtered solution was then loaded onto a size exclusion column (either Superose 12 or Superdex 75, Pharmacia) and eluted with 50 mM sodium phosphate, 150 mM NaCl, pH 7.0 buffer. FIG. 2A shows the elution profile From the purification of the PEG-IFN-β conjugate on a Superose 12 size exclusion chromatography column. The peaks were collected and analyzed with SDS-PAGE (FIG. 3). The fractions containing the PEG-IFN-β conjugate were pooled together and concentrate was then reloaded to the same size exclusion column to further purify the PEG-IFN-β conjugate due to the close proximity of the "native" IFN-β peak (FIG. 2B). This procedure was repeated (third dass) to ensure purity (FIG. 2C). FIG. 4 and FIG. 5 show the Capillary Electrophoresis graph and the MALDI MS spectrum, respectively, of the purified PEG-IFN-β conjugate.

Modification of IFNT-β with mPEG$_{30K}$-OPSS

Recombinant human IFN-β was provided is stable in solution at 0.3 mg/ml in 50 mM sodium acetate buffer, pH 3.6. Approximately 36 mg of mPEG$_{30K}$-OPSS in 3 ml deionized H$_2$O was added to 3 ml of IFN-β at 0.36 mg/ml (1.08 mg, 4.9-×10$^{-8}$ moles) and the two were allowed to react in a polypropylene vial for 2 hours at 50° C. The reaction mixture was analyzed with capillary electrophoresis for extent of modification. Typical yields for this reaction are <30%. The solution was then loaded onto a size exclusion column (Superose 12, Pharmacia) and eluted with 50 mM sodium phosphate, 150 mM NaCl, pH 7.0 buffer. The peaks were collected and analyzed with SDS-PAGE for their contents.

EXAMPLE 2

Biological Activity of the PEG-IFN-β Conjugate

To assess the effects of PEGylation on the anti-viral activity of human recombinant IFN-β, human WISH amniotic cells were preincubated with either freshly prepared IFN-β (same lot as used for PEGylation) or PEG-IFN-β conjugate. The IFN-β-mediated anti-viral activity, as measured by the WISH-VSV cytopathicity assay, was determined according to an anti-viral WISH bioassay developed based on the protocol of Novick et al., *J. Immunol.*, 129:2244-2247 (1982). The materials used in this WISH assay is as follows:

WISH cells (ATCC OCL 25)

Vesicular Stomatitis Virus stocks (ATCC V-520-001-522), stored at −70° C.

IFN-β, human recombinant, InterPharm Laboratories LTD (32,075-type, Batch # 205035), 82×10⁶ IU/ml, specific activity: 222×10⁶ IU/mg PEG-IFN-β conjugate as prepared in Example 1 and maintained in PBS, pH 7.4

WISH Growth medium (MEM high glucose with Earls salts+10% FBS+1.0% L-glutamine+Penicillin/Streptorycin (100 U/ml, 100 μ/ml)

WISH Assay medium (MEM high glucose with Earls salts+5% FES+1.0% L-glutamine+Penicillin/Streptomycin (100 U/ml, 100 μ/ml)

MTT at 5 mg/ml in PBS, stored at minus 70° C. The protocol for the WISH assay is as follows:

Dilute the IFN-β samples to 2× the starting concentration in WISH assay medium.

Make three-fold dilutions of IFN-β samples in WISH assay medium in flat-bottomed 96-well plate so that each well contains 50 μl of diluted IFN-β sample (some control wells receive 50 μl of WISH assay medium only).

Harvest log growth phase WISH cells with trypsin/EDTA solution, wash in WISH assay medium, and bring to a final concentration of 0.8×10⁶ cells/ml.

Add 50 μl of WISH cell suspension (4×10⁴ cells per well) to each well. Final concentration of IFN-β exposed to the cells is now 1×.

After incubation for 24 hours in a 5% $CO_2$ humidified incubator, 50 μl of a 1:10 dilution (in WISH assay medium) of VSV stock (a dose predetermined to lyse 100 percent of WISH cells within 48 hours) is added to all wells except for the no 15 virus control wells (these receive an equal volume of assay medium only).

After an additional 48 hours, 25 μl of MTT solution is added to all wells, after which plates are incubated for an additional 2 hours in an incubator.

The contents of the wells are removed by plate inversion, and 200 μl of 100% ethanol is added to the wells.

After 1 hour, the plates are read at 595 nm using the Soft max Pro software package and Spectramax spectrophotometer system (Molecular Devices).

TABLE 1

Antiviral Activity of PEGylated and Mock-PEGylated IFN-beta Samples

| IFN-beta Sample* | $EC_{50}$** |
|---|---|
| PEG-IFN-β conjugate | 3.9 +/− 0.7 pg/ml |
| IFN-β | 16.4 +/− 1.0 pg/ml |

*Stock concentrations of IFN-β in samples determined by amino acid analysis.
**$EC_{50}$ (+/−S.D.) was determined by software program Microcal Origin 4.1

Figure 6:
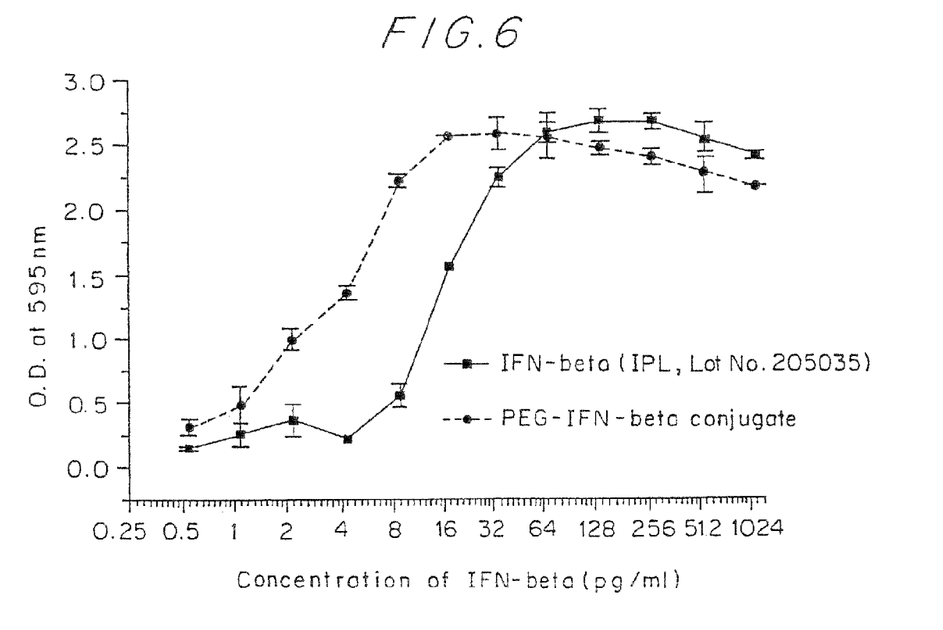
FIG. 6 shows a comparison between the anti-viral activity of "native" IFN-β and of PEG-IFN-β conjugate. WISH cells were incubated with indicated concentrations of IFN-β samples for 24 hours prior to challenge with cytopathic dose of vesicular stomatitis virus. The cytopathic effect was determined after an additional 48 hours by MTT conversion.

As demonstrated in FIG. 6 and Table 1 above, the PEG-IFN-β conjugate maintained a level of anti-viral activity superior to that of the freshly prepared parental lot of IFN-β. The observation that the PEG-IFN-β conjugate has approximately 4-fold higher bioactfvity than that of freshly prepared IFN-β may be also a consequence of the increased stability of the PEG-IFN-β conjugate with respect to the "native" IFN-β after addition of WISH cell assay medium.

EXAMPLE 3

In Vitro Assays of the Relative Activity of PEG-IFN Samples

Relative bioactivity of PEG[30 kD]-IFN-β and PEG[2×20 kD]-IFN-β was determined by WISH assay using the standard protocol described in Example 2 (Table 2) Three independent assays were performed by three different individuals at separate times.

TABLE 2

Relative antiviral activity of PEG-IFN-β

| | Relative Interferon Activity* (from three studies) | | | |
|---|---|---|---|---|
| Sample | Assay 1 | Assay 2 | Assay 3 | Average (S.D.) |
| PEG[30 kD]-IFN-β | 3.2 × higher | 3.1 × higher | 1.8 × higher | 3.0 × (0.78) higher |
| PEG[2 × 20 kD]-IFN-β | 4.2 × higher | 1.3 × higher | 0.85 × higher | 2.1 × (1.8) higher |

*EC50 doses compared with standard IFN-β included in each assay.
**Comparison based on IFN-β concentration of 330 ug/ml. Stock concentrations of PEG[30 kD]-IFN-β (5.41 ug/ml) and PEG[2 × 20 kD]-IFN-β (6.86 ug/ml) were determined by AAA.

Figure 7:
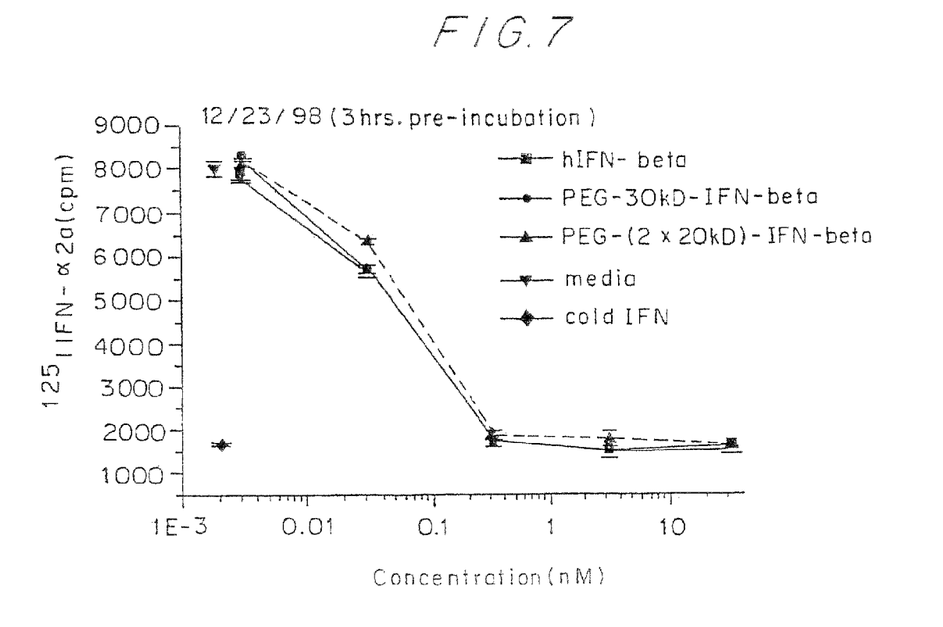
FIG. 7 shows the binding proflie of IFN-β and PEG-IFN in Daudi cells.

The binding of PEG-IFN-β to its receptor on cells was evaluated in the presence of a fixed amount of $^{125}$I-IFN-α2a. IFN-α2a was radiolabeled with $^{125}$I using the chloramine T method. The $^{125}$I bound IFN-α2a was removed from free iodine by running the reactants through a Sephadex G25 column and pooling the protein containing fractions (Pharmacia). $^{125}$I-IFN-α2a was quantified by an IFN-α2a ELISA assay (Diosource, USA) and the specific activity was determined. Daudi cells grown in the exponential phase of growth were harvested and 2×10⁶ cells were incubated with 0.5 nM $^{125}$I-IFN-α2a for 3 hours ao room temperature in the presence of different concentrations of PEG-IFN-β or IFN-α2a diluted in an assay buffer which is RPMI 1540 containing 2% fetal bovine serum and 0.1% sodium azide. At the end of the incubation, the cells were spun through-a layer of phthalate oil and the cell bound radioactivity was counted on the gamma counter. Furthermore, the binding of PEG[30 kD]-IFN-β and PEG[2×20 kD]-IFN-β to the receptor were very similar or close to the binding activity of IFN-β as shown in FIG. 7.

In addition, relative activity was determined in a Daudi cell (human B cell lymphoma) anti-proliferation assay (Table 3). All IFNs were made at a 2× concentration of 200 ng/ml. Samples were diluted three-fold down the length of the late at a final volume of 100 ul. 1×10⁵ cells/well (100 μls) were added to each well and incubated for a total of 72 hours at 37° C. in $CO_2$ humidified incubator. After 48 hours, tritiated ($^3$H) thymidine were added at 1 μCi/well in 20 ul. At the end of the 72 hour incubation, the plate was harvested with the Tomtek Plate Harvester. The results shown in Table 3 indicate that no detectable loss of IFN activity was observed from PPGylation. In fact, the activity was found to be somewhat higher than free IFN-β. This may be due to the formation of inactive aggregates in the free IFN or to the differences in auantitation methods (amino acid analysis for PEG-IFN samples and RP-HPLC for IFN-β)

TABLE 3

Daudi Anti-Proliferation Assay

| | IC$_{50}$dose* | Fold increase vs IFN |
|---|---|---|
| IFN-β (Plate 1) | 1153.1 | — |
| PEG[30 kD]-IFN (71 A) | 695.6 | 1.6X |
| IFN-β (Plate 2) | 1005.8 | — |
| PEG[40 kD]-IFN (71 B) | 629.4 | 1.7X |

*pg/ml

EXAMPLE 4

Pharmacokinetic Studies in Mice

Intravenous Administration

Figure 8:
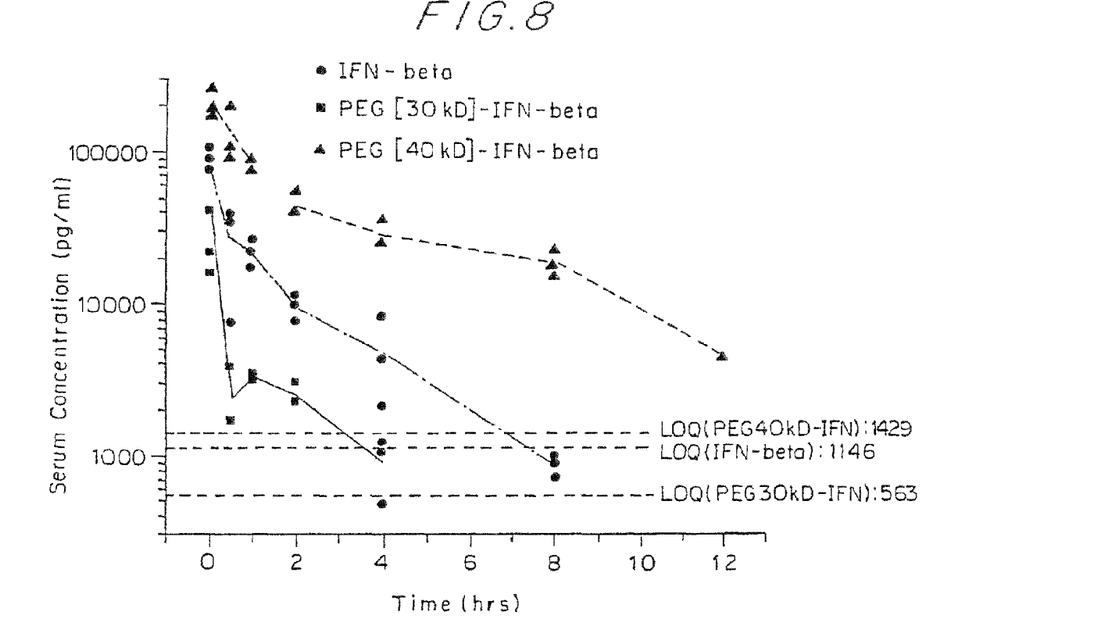
FIG. 8 shows the pharmokinetic profile of IFN-β and PEG-IFN in mice following intravenous administration. The dotted lines indicate assay LOQ for each standard curve.

Mice were injected with 100 ng of IFN-β, PEG[30 kD]-IFN-β or PEG[2×20 kD]-IFN-β and blood was removed at indicated times thereafter. Serum concentrations of IFN-β were determined by IFN-β-specific ELIAS (Toray Industries) and the results are shown in FIG. 8. Twenty-eight female B6D2F1 strain mice (6-8 wks) (approximately 20 g each) were separated into four groups as follows: Group 1 contained nine mice injected with a 200 ul single bolus of 500 ng/ml human IFN-β (final dose of 100 ng/mouse); Group 2 (nine mice) received 200 ul of an equivalent mass of PEG30 kD-IFN-β; Group 3 received 200 ul of an equivalent mass of PEG(2×20 kD)-IFN-β; and Group 4 is a group of three uninjected mice serving as a negative controlB lood samples (approximately 200 ul/sample) were collected at nine indicated times by disruption of the retro-orbital venous plexus with a capillary tube. Blood samples were allowed to clot for 1 hr at room temperature, rimmed and microcentrifuged. Sera removed therefrom were stored at −70° C. until all samples were collected. Sera were assayed for the presence of bioactive human IFN-β using the Toray assay. The results indicate that the area under the curve (AUC) is markedly enhanced in the PEG-IFN samples versus free IFN-beta and that PEG-IFN samples versus free IFN-β and that PEG [2×20 kD]-IFN-β is superior to the PEG[30 kD]-IFN-β.

Subcutaneous Administration

Figure 9:
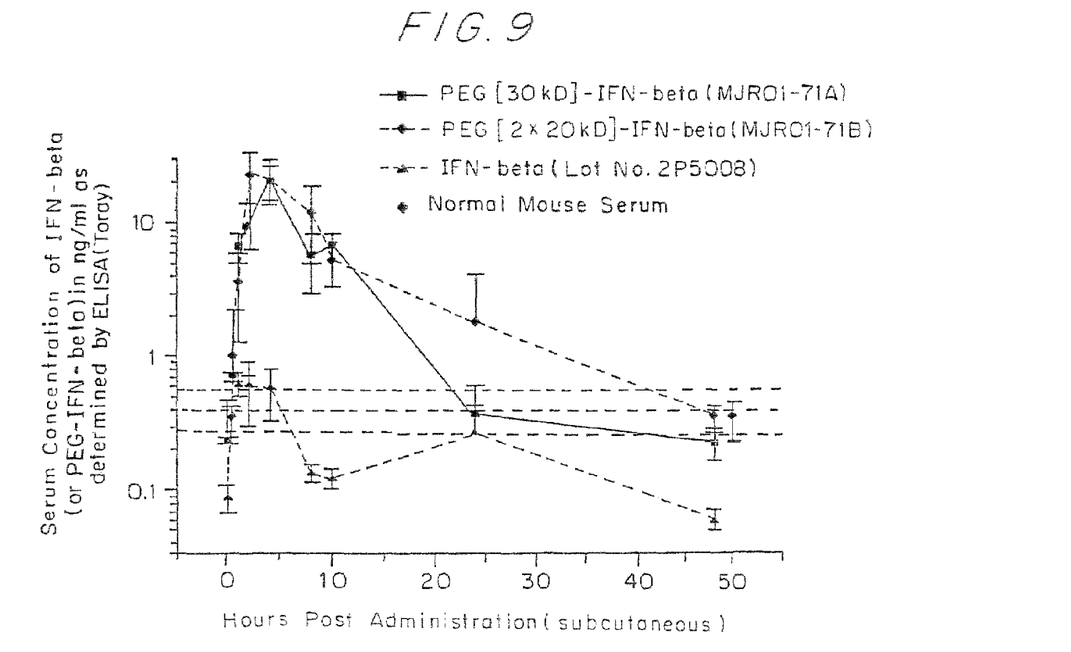
FIG. 9 shows the pharmokinetic profile of IFN-β and PEG-IFN in mice following subcutaneous administration. The dotted lines indicate assay LOQ for each standard curve.

Mice were injected subcutaneously with IFN-β and PEG-IFN (100 ng/mouse). FIG. 9 demonstrates that the total area under the curve (AUC) is dramatically enhanced for the PEG-IFN samples as compared with free IFN-β. The pharmacokinetic studies are consistent with the PEG-IFN samples having a longer half-life and increased AUC.

EXAMPLE 5

Attachment of Low Molecular Weight PEG Moiety to Polypeptide

Tagging Interferon-beta with OPSS-PEG$_{2K}$-Hydrazide

Recombinant human interferon-β was provided in solution at 0.33 mg/ml in 50 mM sodium acetate buffer, pH 3.8. Approximately 3.6 mg (40 mole excess to moles of protein) of the heterobifunctional PEG reagent, OPSS-PEG$_{2k}$-hydrazide, in 2 ml deionized water was added to 3 ml of IFN-β at 0.33 mg/ml (0.99 mg) and the two were allowed to react in a polypropylene vial for 1 hour at 45° C. The reaction mixture was then analyzed with capillary electrophoresis to determine the extent of modification. Typical yields ranged from 90-97%; that depended on the purity of the interferon β and PEG reagent. The solution was next loaded onto a size exclusion column (Superdex 75, Pharmacia) and eluted with 5 mM sodium phosphate, 150 mM NaCl, pH 7.0 buffer. The peaks were collected and analyzed with SDS-PAGE. The monoPEGylated interferon-β fractions were pooled together than used in a further modification step with high molecular weight PEG.

Tagging Interferon-β with (OPSS)$_2$-PEG$_{3400}$

Recombinant human interferon-β was provided in solution at 0.33 mg/ml in 50 m sodium acetate buffer, pH 3.8. Approximately 6.1 mg (40 mole excess to moles of protein) of the homobifunctional PEG reagent, (OPSS)$_2$-PEG$_{3400}$, in 2 ml deionized water was added to 3 ml of interferon-β at 0.33 mg/ml (0.99 mg) and the two were allowed to react in a polypropylene vial for 2 hours at 50° C. The reaction was monitored with non-reducing SDS-PAGE and the final reaction mixture was analyzed with capillary electrophoresis to determine the extent of modification. Typical modifications for this reaction with interferon-β were >95%. The solution was then loaded onto a size exclusion column (Superdex 75, Pharmacia) and eluted with 50 mM sodium phosphate, 150 mM NaCl, pH 7.0 buffer. The peaks were collected and analyzed with SDS-PAGE for their contents. The monoPEGylated interferon-β fractions were combined.

EXAMPLE 6

Attachment of Second PEG Moiety to Low Molecular Weight PEGylating Polypeptide

Modification of IFN-S-S-PEG$_{2k}$-Hydrazide with mPEG$_{30k}$-Aldehyde (ALD)

To the combined fractions of IFN-S-S-PEG$_{2k}$-Hydrazide in Example 5 was added mPEG$_{30k}$-ALD in a 20 mole excess to protein. The reaction was conducted at room temperature (25≅ C.) for 4 hours and a sample was added to a size exclusion column (Superose 6, Pharmacia) to determine modification yield. The modification yield of this reaction was typically >80% depending upon the purity of the PEG reagent and reaction conditions.

Having now fully described this invention it will be appreciated that by those skilled in the art that the same can be performed within a wide range so equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

All references cited herein, including journal articles or abstracts, published or unpublished U.S. or foreign patent applications, issued U.S. or foreign patents, or any other references, are entirely incorporated by reference herein, including all data, tables, figures, and text presented in the cited references. Additionally, the entire contents of the references cited within the references cited herein are also entirely incorporated by reference.

Reference to known method steps, conventional method steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to he interpreted by the skilled artisan in light of the teachings and guidance presented herein, in combination with the knowledge of one of ordinary skill in the art.

What is claimed is:

1. A method for producing a polyol-interferon-β conjugate having a polyol moiety covalently bound to $Cys^{17}$ of human interferon-β(fibroblast interferon), comprising:
reacting interferon-β with a thiol-reactive polyol agent to site specifically and covalently attach a polyol moiety to $Cys^{17}$ of human interferon-β [fibroblast interferon] to produce a polyol-interferon-β [human fibroblast interferon] conjugate; and recovering the produced polyol-interferon-β conjugate.

2. The method according to claim 1, wherein the thiol-reactive polyol agent is a thiol-reactive PEGylating agent.

3. The method according to either claim 1 or claim 2, wherein the thiol-reactive polyol agent is mono-methoxylated.

4. The method according to either claim 1 or claim 2, wherein the thiol-reactive polyol agent is bifunctional.

5. The method according to either claim 1 or claim 2, wherein the thiol-reactive polyol agent is a polyol derivative having a functional group selected from the group consisting of orthopyridyl disulfide, vinyl sulfone, maleimide, and iodoacetimide.

6. The method according to either claim 1 or claim 2, wherein the thiol-reactive polyol agent is an orthopyridyl disulfide derivative of a mono-methoxylated polyol.

7. The process according to claim 1, wherein the reacting step is carried out at an acidic pH where interferon-ss is stable.

* * * * *